United States Patent
Fedan et al.

(10) Patent No.: US 7,907,999 B2
(45) Date of Patent: Mar. 15, 2011

(54) APPARATUS AND METHOD FOR MEASURING PHYSIOLOGICAL CHARACTERISTICS OF AN INTACT TRACHEA IN VITRO

(75) Inventors: Jeffrey S. Fedan, Morgantown, WV (US); Yi Jing, Morgantown, WV (US); Michael Van Scott, Greenville, NC (US)

(73) Assignees: The United States of America as represented by the Secretary of the Department of Health and Human Services, Washington, DC (US); East Carolina University, Greenville, NC (US); Centers for Disease Control and Prevention, Atlanta, GA (US)

( * ) Notice: Subject to any disclaimer, the term of this patent is extended or adjusted under 35 U.S.C. 154(b) by 887 days.

(21) Appl. No.: 11/655,635

(22) Filed: Jan. 19, 2007

(65) Prior Publication Data
US 2007/0170928 A1    Jul. 26, 2007

Related U.S. Application Data

(60) Provisional application No. 60/762,465, filed on Jan. 25, 2006.

(51) Int. Cl.
*A61B 5/05* (2006.01)
(52) U.S. Cl. ........................................ 600/547; 600/560
(58) Field of Classification Search .................. 600/547
See application file for complete search history.

(56) References Cited

U.S. PATENT DOCUMENTS

| | | | |
|---|---|---|---|
| 4,245,643 | A | 1/1981 | Benzing, III et al. |
| 5,063,937 | A | 11/1991 | Ezenwa et al. |
| 5,397,452 | A | 3/1995 | Buck et al. |
| 5,490,916 | A | 2/1996 | Hall |
| 5,833,825 | A | 11/1998 | Otten et al. |
| 6,465,205 | B2 | 10/2002 | Hicks, Jr. |
| 6,823,212 | B2 | 11/2004 | Pinyayev |
| 6,865,409 | B2 | 3/2005 | Getsla et al. |
| 6,922,586 | B2 | 7/2005 | Davies |

(Continued)

FOREIGN PATENT DOCUMENTS
WO    WO 99/48422    9/1999

OTHER PUBLICATIONS

Y. Jing et al. "Epithelial bioelectric and muscle mechanical effects of pharmacological agents in a newly-developed guinea-pig isolated trachea perfusion apparatus."*

(Continued)

*Primary Examiner* — Max Hindenburg
*Assistant Examiner* — Michael C Stout
(74) *Attorney, Agent, or Firm* — Klarquist Sparkman, LLP

(57) ABSTRACT

Apparatus and methods for measuring smooth muscles responses (relaxation and contraction), transepithelial potential difference, and/or transepithelial impedance of an intact trachea in vitro. In particular embodiments, the apparatus includes a perfusion device on which an extracted, intact trachea is mounted. The perfusion device and the trachea are immersed in an extraluminal bath, which is isolated from the perfusion liquid flowing through the trachea. A set of voltage-sensing electrodes is provided for measuring the transepithelial potential difference across the trachea wall. A set of current electrodes is provided for inducing an electrical current to flow across the trachea wall in order to determine transepithelial impedance.

22 Claims, 12 Drawing Sheets

U.S. PATENT DOCUMENTS

2002/0173041 A1 11/2002 Canas et al.
2004/0265302 A1 12/2004 Nadel et al.

OTHER PUBLICATIONS

Hjoberg et al. "Hyperosmolarity reduces the relaxins potency of nitric oxide donors in guinea-pig trachea." British Jounal of Pharmacology (1999) 127, 391-396.*

Durand et al. "Volume Flow, Hydraulic Conductivity and Electrical Properties Across Bovine Tracheal Epithelium in vitro: Effect of Histamine," Pflugers Arch (1981) 392:40-45.*

Gudrun Baersch et al. "A New Bioassay to Study Contractile and Relaxant Effects of PGE on Perfused Guinea Pig Trachea," Journal of Pharmacological and Toxicological Methods 36, 63-68 (1996).*

Blouquit et al., "Effects of Endothelin-1 on Epithelial Ion Transport in Human Airways," Am. J. Respir. Cell. Mol. Biol., 29(2): 245-51, Mar. 6, 2003.

Cloutier et al., "Electrophysiological Properties of the Airway," Am.. J. of Pathology, 164: 1849-1856, May 2004.

Davidson et al., "A Primary Culture Model of Differentiated Murine Tracheal Epithelium," Am. J. Physiol. Lung. Cell. Mol. Physiol., 279: L766-L778, 2000.

Dortch-Carnes, et al., Changes in Smooth Muscle Tone During Osmotic Challenge in Relation to Epithelial Bioelectric Events in Guinea Pig Isolated Trachea, The Journal of Pharmacology and Experimental Therapeutics, 289(2): 911-917, 1999.

Jeffrey S. Fedan, bio, www.hsc.wvu.edu/som/physio/Faculty/fedan. htm, (2 pages).

Fedan et al., "Influence of Epithelium on the Reactivity of Guinea Pig Isolated, Perfused Trachea to Bronchoactive Drugs," The Journal of Pharmacology and Experimental Therapeutics, 262(2): 741-750, 1992.

Fedan et al., "Effect of Ozone Treatment on Airway Reactivity and Epithelium-Derived Relaxing Factor in Guinea Pigs," The Journal of Pharmacology and Experimental Therapeutics, 293(3): 724-734, 2000.

Fedan et al., "Hyperosmolar Solution Effects in Guinea Pig Airways. I. Mechanical Responses to Relative Changes in Osmolarity," The Journal of Pharmacology and Experimental Therapeutics, 308(1): 10-18, 2004.

Fedan et al., "Hyperosmolar Solution Effects in Guinea Pig Airways. IIII. Studies on the Identify of Epithelium Derived Relaxing Factor in Isolated Perfused Trachea Using Pharmacological Agents," The Journal of Pharmacology and Experimental Therapeutics, 308(1): 30-36, 2004.

Fortner et al., Chloride Channel Function is Linked to Epithelium-Dependent Airway Relaxation, Am. J. Physiol. Lung Cell. Mol. Physiol., 280:L334-L341, 2001.

Goto et al., "In Vitro Reconstitution of the Tracheal Epithelium," Am. J. Respir. Cell Mol. Biol., 20: 312-318, 1999.

Jing et al., abstract, "Epithelial Bioelectric and Muscle Mechanical Effects of Pharmacological Agents in a Newly-Developed Guinea-pig Isolated Trachea Perfusion Apparatus," Mar. 31, 2005, 1 page.

Jing et al., poster, "Epithelial Bioelectric and Muscle Mechanical Effects of Pharmacological Agents in a Newly-Developed Guinea-pig Isolated Trachea Perfusion Apparatus" presented at the Experimental Biology 2005 meeting, San Diego, CA, Mar. 31-Apr. 5, 2005.

Johnston et al., "Hyperosmolar Solution Effects in Guinea Pig Airways. IV. Lipopolysaccharide-Induced Alterations in Airway Reactivity and Epithelial Bioelectric Responses to Methacholine and Hyperosmolarity," The Journal of Pharmacology and Experimental Therapeutics, 308(1): 37-46, 2004.

Kao et al., "Ablation of the SERCA3 Gene Alters Epithelium-Dependent Relaxation in Mouse Tracheal Smooth Muscle," American Physiological Society, L264-L270, 1999.

Munakata et al., "Osmotic Stimuli Induce Epithelial-Dependent Relaxation in the Guinea Pig Trachea," The American Physiological Society, 466-471, 1988.

Munakata et al., "Protective Role of Epithelium in the Guinea Pig Airway," The American Physiological Society, 1547-1552, 1989.

Pascual et al., "Epoxygenase Metabolites of Arachidonic Acid Affect Electrophysiologic Properties of Rat Tracheal Epithelial Cells," The Journal of Pharmacology and Experimental Therapeutics, 286(2): 772-779, 1998.

Physiologic Instruments, Inc., website, www.physiologicinstruments.com, Physiologic Instruments for Medical Research, 3 pages.

Saez et al., "Peripheral Airway Smooth Muscle Mechanics in Obstructive Airways Disease," Am. J. Respir. Crit. Care Med., 161:910-917, 2000.

Saez et al., "Tissue Elastance Influences Airway Smooth Muscle Shortening: Comparison of Mechanical Properties Among Different Species," Can. J. Physiol. Pharmacol./Rev. Can. Physiol. Pharmacol., 80(9): 865-871, 2002.

The State University of New York, University Buffalo Office of Science, Technology Transfer & Economic Outreach, "Composite Culture on In-Vitro Model of Tracheal Lumen," UB Dockets 5413, 5546, 5558, 5764; 4 pages.

World Precision Instruments, website, www.wpiinc.com/WP_Web/Tissue_Cell/USSING_System.html, Ussing System for Electrophysiological Investigation of Epithelial Transport (5 pages).

Wu et al., "Stimulation of the $BK_{ca}$ Channel in Cultured Smooth Muscle Cells of Human Trachea by Mognolol," Thorax, 57: 67-74, 2002.

Wu et al., "Hyperosmolar Solution Effects in Guinea Pig Airways. II. Epithelial Bioelectric Responses to Relative Changes in Osmolarity," The Journal of Pharmacology and Experimental Therapeutics, 308(1): 19-29, 2004.

Yang et al., "Role of the Epithelium in Airway Smooth Muscle Responses to Relaxant Agonists," The American Physiological Society, 1434-1440, 1991.

* cited by examiner

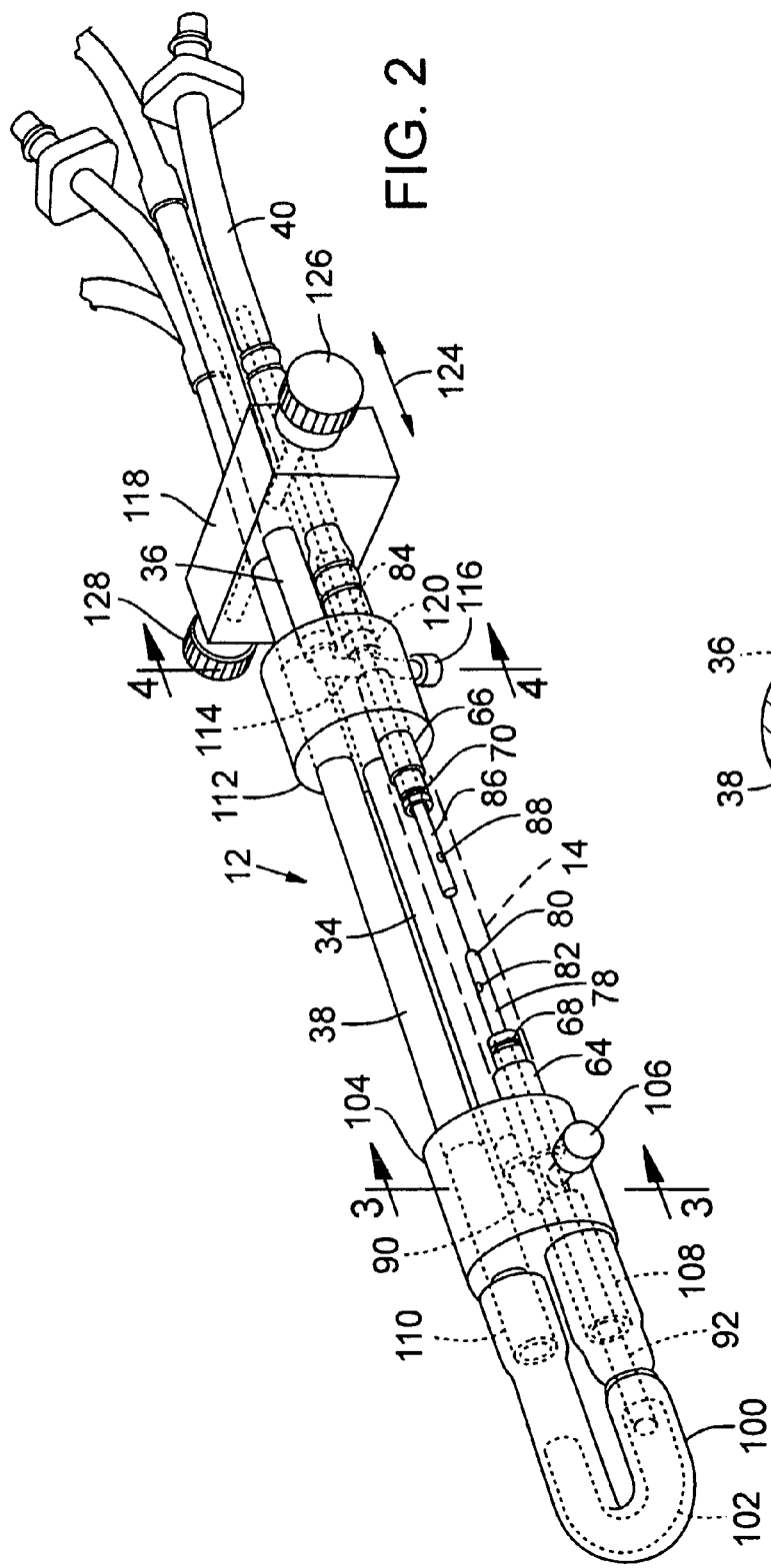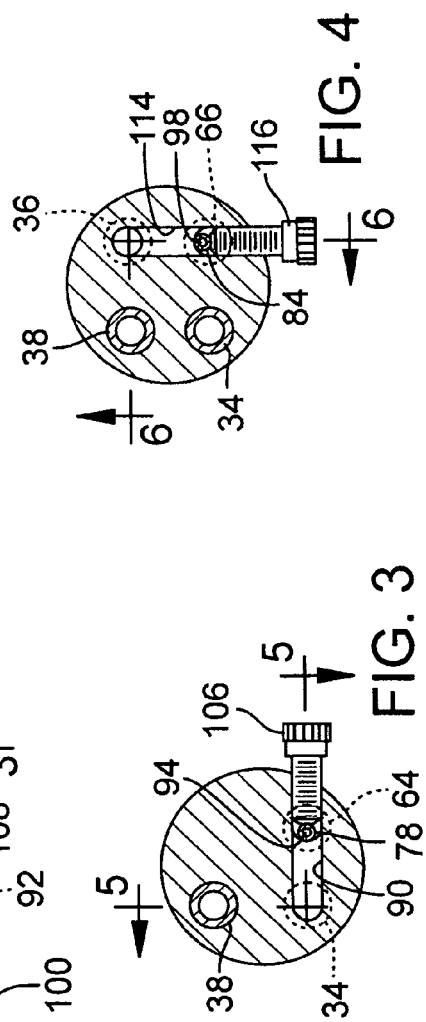

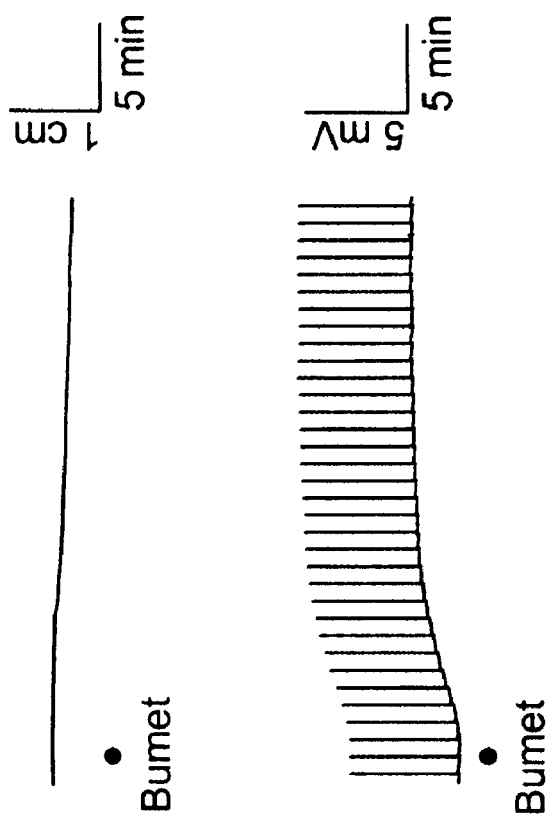
FIG. 10A
FIG. 10B
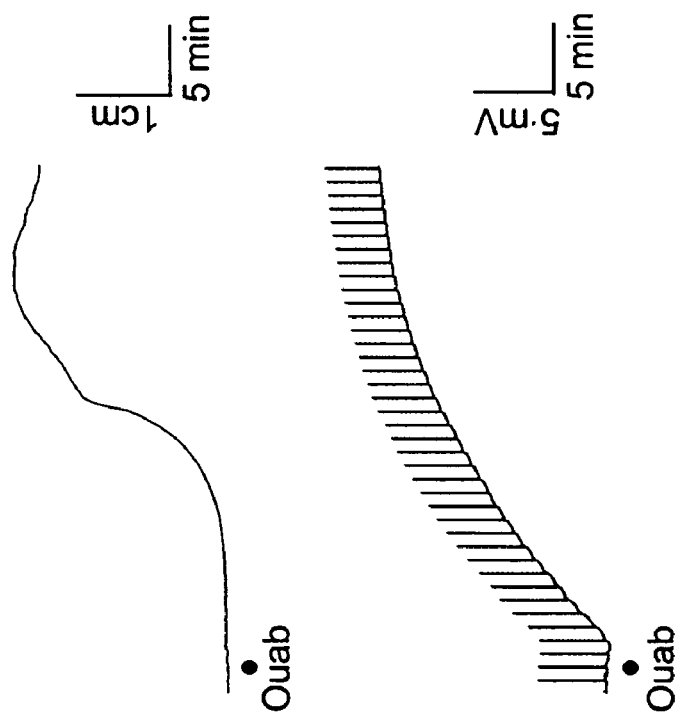
FIG. 10C
FIG. 10D

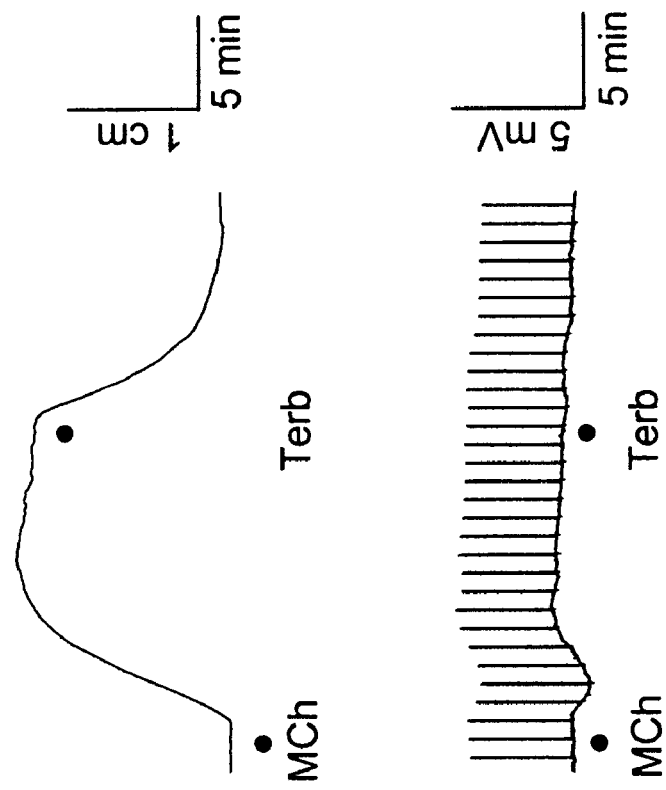
FIG. 12A
FIG. 12B
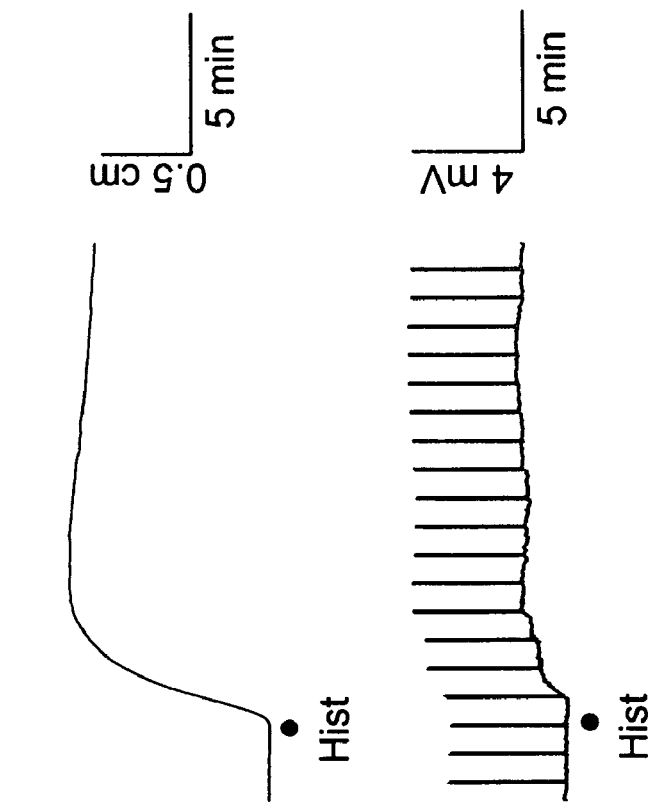
FIG. 12C
FIG. 12D

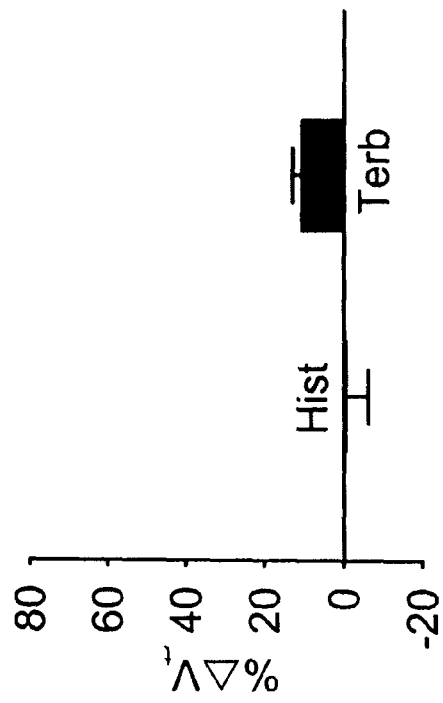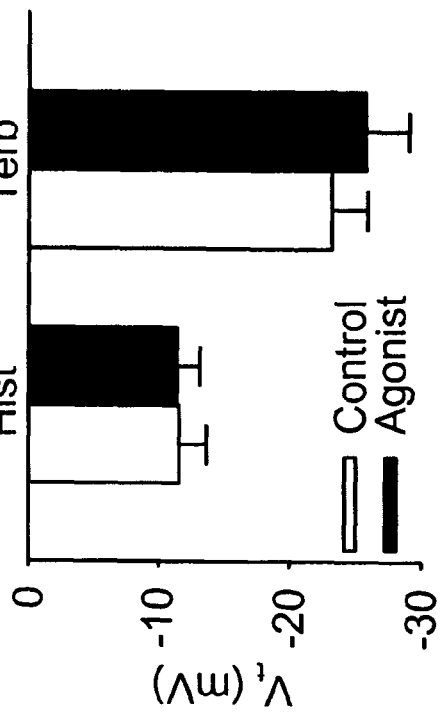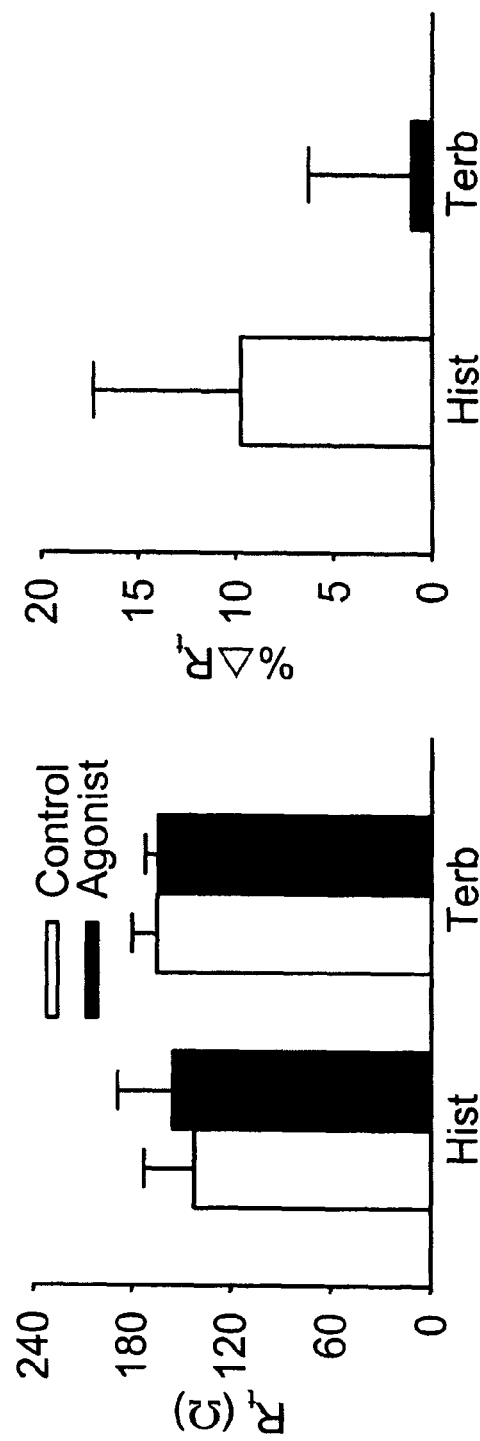
FIG. 13A  FIG. 13B  FIG. 13C  FIG. 13D

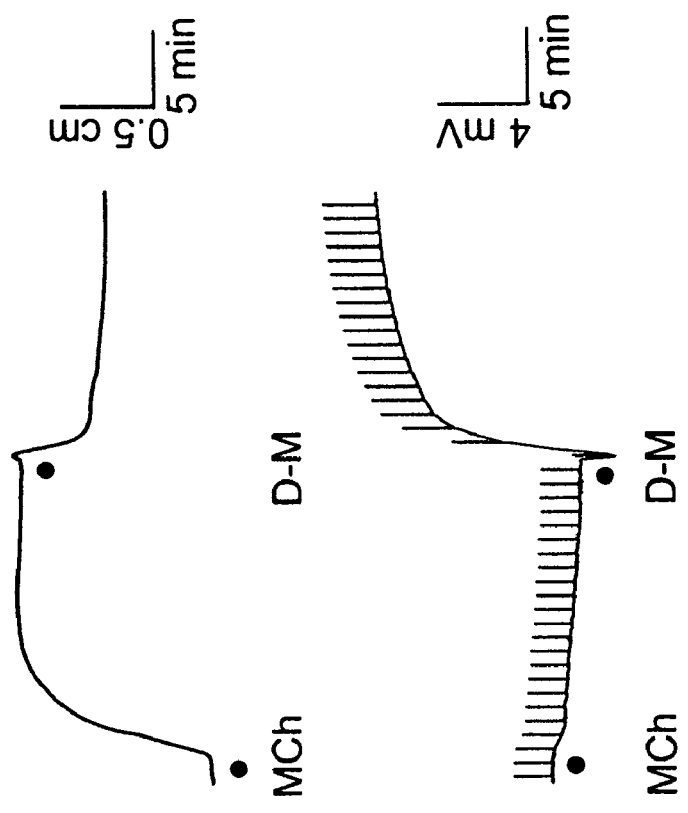
FIG. 14A
FIG. 14B
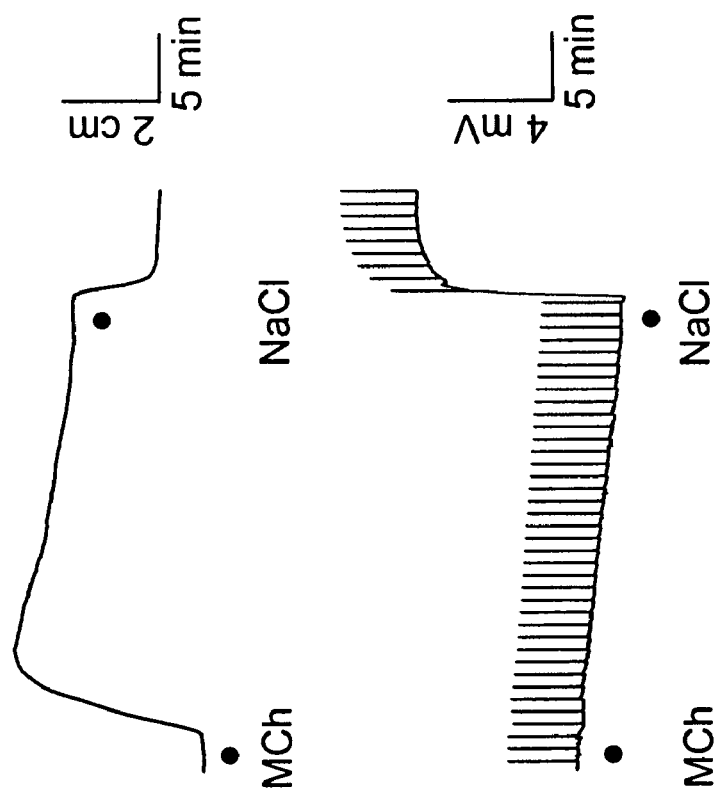
FIG. 14C
FIG. 14D

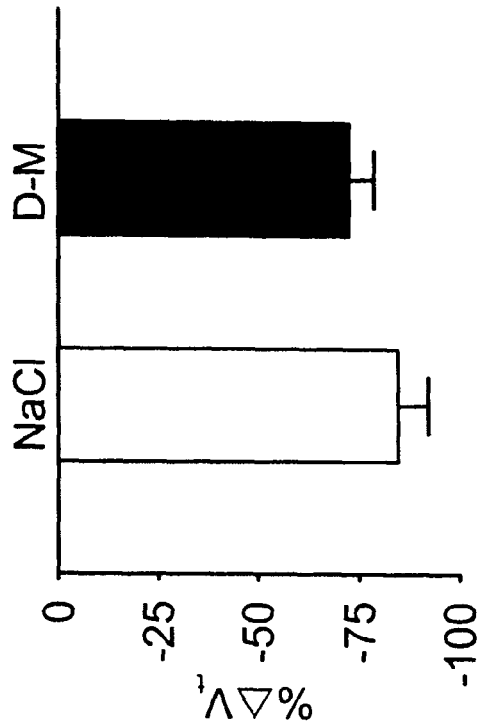
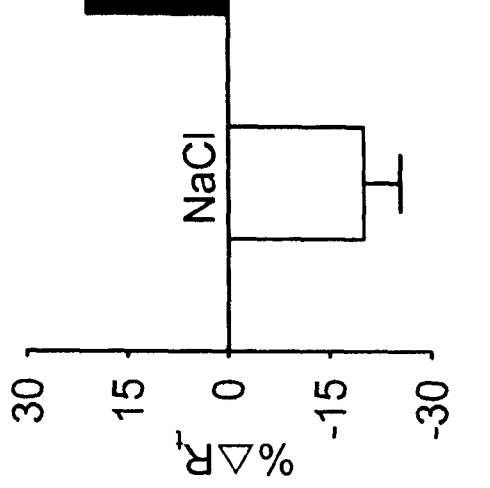
FIG. 15A
FIG. 15B
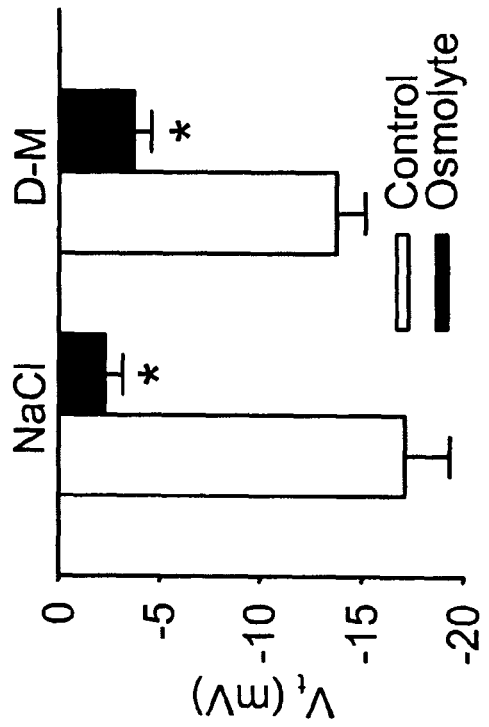
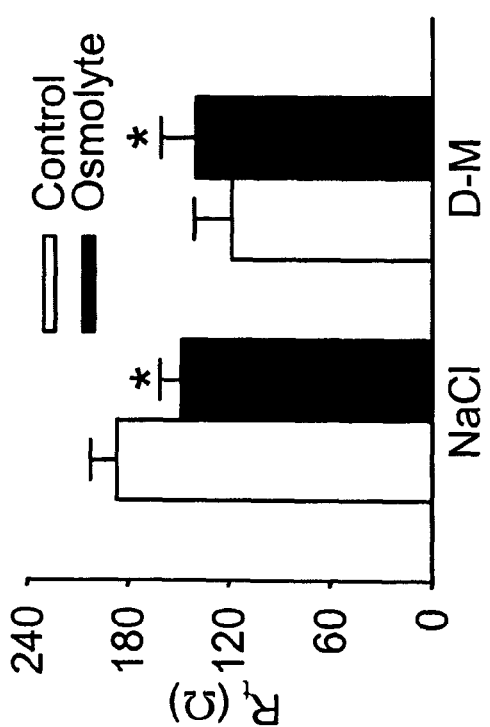
FIG. 15C
FIG. 15D

APPARATUS AND METHOD FOR MEASURING PHYSIOLOGICAL CHARACTERISTICS OF AN INTACT TRACHEA IN VITRO

CROSS-REFERENCE TO RELATED APPLICATION

The present application claims the benefit of U.S. Provisional Application No. 60/762,465, filed Jan. 25, 2006, which is incorporated herein by reference.

ACKNOWLEDGMENT OF GOVERNMENT SUPPORT

This invention was made by The National Institute for Occupational Safety and Health, Centers for Disease Control and Prevention, an agency of the United States Government.

FIELD

The present invention concerns an apparatus and method for measuring physiological characteristics of an intact trachea in vitro, and in particular, simultaneously measuring epithelial bioelectric properties and muscle responses of the trachea.

BACKGROUND

Investigation of the mechanisms of lung diseases, such as asthma and cystic fibrosis, involves understanding the roles of the smooth muscle and the epithelium of the airway (trachea). The smooth muscle controls the airway diameter, while the epithelium regulates ionic composition of the liquid lining the airway through electrogenic ion transport and releases factors that regulate the ability of the smooth muscle to contract. Various techniques and apparatus are known for stimulating an intact trachea or a tracheal segment in vitro and for measuring smooth muscle activity and bioelectric properties of the epithelium in response to the stimuli.

One known technique for measuring the contraction and relaxation of the airway smooth muscle involves mounting an intact trachea to a perfusion device for flowing a perfusion liquid through the trachea. The perfusion device has an inlet cannula extending into one end of the trachea and an outlet cannula extending into the opposite end of the trachea. A differential pressure device fluidly connected to the cannulas measures the differential pressure of the perfusion liquid flowing through the trachea (e.g., the inlet pressure minus the outlet pressure), which is a direct index of the airway diameter. The inner epithelial surface or the outer serosal surface is stimulated by adding agents to the perfusion liquid or an extraluminal bath in which the trachea is disposed. The differential pressure device is used to detect changes in the airway diameter in response to the stimuli. A drawback of this technique is that there is no provision for measuring bioelectric properties of the epithelium, such as the electrical potential across the epithelium (transepithelial potential difference) and the impedance of the epithelium (transepithelial impedance).

In an improvement of the foregoing technique, the perfusion device and trachea are placed in an extraluminal bath containing a voltage electrode. Another voltage electrode is placed in the perfusion line supplying the perfusion liquid to the trachea. The voltage electrodes are used to measure the transepithelial potential difference of the trachea. As described above, a differential pressure device can be used to measure the differential pressure of the perfusion liquid flowing through the trachea. While an improvement of prior devices, this technique suffers from the disadvantage that there is no provision for measuring the transepithelial impedance of the trachea.

A common technique for simultaneously measuring the transepithelial potential and transepithelial impedance of a trachea involves placing a small, flattened strip of trachea in an in vitro apparatus known as an "Ussing" chamber. The chamber has separate ports for connecting voltage electrodes and current electrodes. The voltage electrodes measure the transepithelial potential difference of the trachea segment, while the current electrodes pass a current through the trachea segment to permit measurement of the transepithelial impedance. Unfortunately, this technique cannot be used for measuring smooth muscle activity of the trachea. Moreover, the cylindrical tracheal wall becomes distorted when it is flattened and clamped inside the Ussing chamber.

Heretofore, prior devices have not allowed for the measurement of smooth muscle activity, transepithelial potential difference and transepithelial impedance of a single trachea preparation. Accordingly, there is a continuing need for improved apparatus and methods for measuring characteristics of a trachea.

SUMMARY

The present disclosure concerns an apparatus and methods for simultaneously measuring smooth muscles responses (relaxation and contraction), transepithelial potential difference, and/or transepithelial impedance of an intact trachea in vitro. In particular embodiments, the apparatus includes a perfusion device on which an extracted, intact trachea is mounted. The perfusion device allows the trachea to be extended to its original, in situ length, and is configured to establish a flow of perfusion liquid through the lumen of the trachea. The perfusion device and the trachea are immersed in an extraluminal bath, which is isolated from the perfusion liquid flowing through the trachea.

A set of voltage-sensing electrodes is provided for measuring the transepithelial potential difference across the trachea wall. The set of voltage-sensing electrodes includes at least a first voltage-sensing electrode placed in electrical continuity with the perfusion liquid in the trachea and a second voltage-sensing electrode immersed in the extraluminal bath. A set of current electrodes is provided for inducing an electrical current to flow across the trachea wall. The set of current electrodes includes at least a first current electrode placed in electrical continuity with the perfusion liquid flowing into the trachea and a second current electrode immersed in the extraluminal bath.

The perfusion device also can include first and second cannulas inserted into the opposite ends of the trachea. The cannulas are fluidly connected to the ports of a differential pressure transducer to permit measurement of the pressure drop of the perfusion liquid flowing through the trachea. The pressure drop is a direct index of airway diameter, and hence is a measurement of smooth muscle relaxation and contraction.

In use and under open circuit conditions, the current electrodes pass an electrical current through the trachea wall and the voltage-sensing electrodes detect the changes in the transepithelial potential difference. Alternatively, the device can be used in a "voltage clamp" (short circuit) mode where calibrated voltage pulses are applied across the trachea wall and the changes in short circuit current are measured. Applying Ohm's Law, the transepithelial impedance can be calculated from the changes in potential difference (using applied current under open circuit conditions) or from the changes in short circuit current (using applied voltage under voltage clamp conditions). An agent can be added to the intraluminal perfusion liquid and/or to the extraluminal bath to evaluate its effect on smooth muscle activity and the transepithelial potential difference and impedance.

Because an agent can be introduced into the trachea lumen, where it must first traverse the epithelium to reach the smooth muscle, or to the outside of the trachea, where there is no hindrance of agents to the smooth muscle, the apparatus permits evaluation of the functional integrity of the epithelium using pharmacological techniques. The apparatus also permits efficient screening of the effects of agents and drugs on airway epithelium and smooth muscle in the same preparation.

The foregoing and other objects, features, and advantages of the invention will become more apparent from the following detailed description, which proceeds with reference to the accompanying figures.

BRIEF DESCRIPTION OF THE DRAWINGS

FIG. 2 is a perspective view of the perfusion device used in the apparatus of FIG. 1 for mounting the trachea.

FIG. 3 is a cross-sectional view of the perfusion device taken along line 3-3 of FIG. 2.

FIG. 4 is a cross-sectional view of the perfusion device taken along line 4-4 of FIG. 2.

FIGS. 10A and 10B are data plots showing the effects of ouabain and bumetanide, respectively, on the differential pressure ($\Delta P$) of the trachea.

FIGS. 10C and 10D are data plots showing the effects of ouabain and bumetanide, respectively, on $V_t$ of the trachea. The vertical lines extending above the data plots show the voltage excursions in response to the application of a calibrated current across the trachea wall.

FIGS. 12A and 12B are data plots showing the effects of histamine and terbutaline, respectively, on $\Delta P$ of the trachea.

FIGS. 12C and 12D are data plots showing the effects of histamine and terbutaline, respectively, on $V_t$ of the trachea. The vertical lines extending above the data plots show the voltage excursions in response to the application of a calibrated current across the trachea wall.

FIGS. 13A-13D are bar graphs summarizing the effects of histamine and terbutaline on $V_t$ and $R_t$ of the trachea.

FIGS. 14A and 14B are data plots showing the effects of hyperosmolarity elicited with NaCl and D-M, respectively, on $\Delta P$ of the trachea.

FIGS. 14C and 14D are data plots showing the effects of hyperosmolarity elicited with NaCl and D-M, respectively on $V_t$ of the trachea. The vertical lines extending above the data plots show the voltage excursions in response to the application of a calibrated current across the trachea wall.

FIGS. 15A-15D are bar graphs summarizing the effects of hyperosmolarity elicited with NaCl and D-M on $V_t$ and $R_t$ of the trachea.

DETAILED DESCRIPTION

As used herein, the singular forms "a," "an," and "the" refer to one or more than one, unless the context clearly dictates otherwise.

As used herein, the term "includes" means "comprises." For example, a device that includes or comprises A and B contains A and B but may optionally contain C or other components other than A and B. A device that includes or comprises A or B may contain A or B or A and B, and optionally one or more other components such as C.

As used herein, an "agent" refers to any composition or substance that affects a biological function of a subject or organ (or part thereof) to which it is administered (in vivo or in vitro). An example of an agent is a pharmaceutical agent, such as a drug or antibiotic, which is given to a subject to alter a physiological condition of the subject or organ, such as a disease.

As used herein, the term "drug" includes any agent administered for a therapeutic (including diagnostic) or research purpose.

As used herein, an "intact" trachea refers to a whole trachea or a tracheal segment having its in situ shape and structure defining a lumen through which a perfusion liquid can flow.

Figure 1:
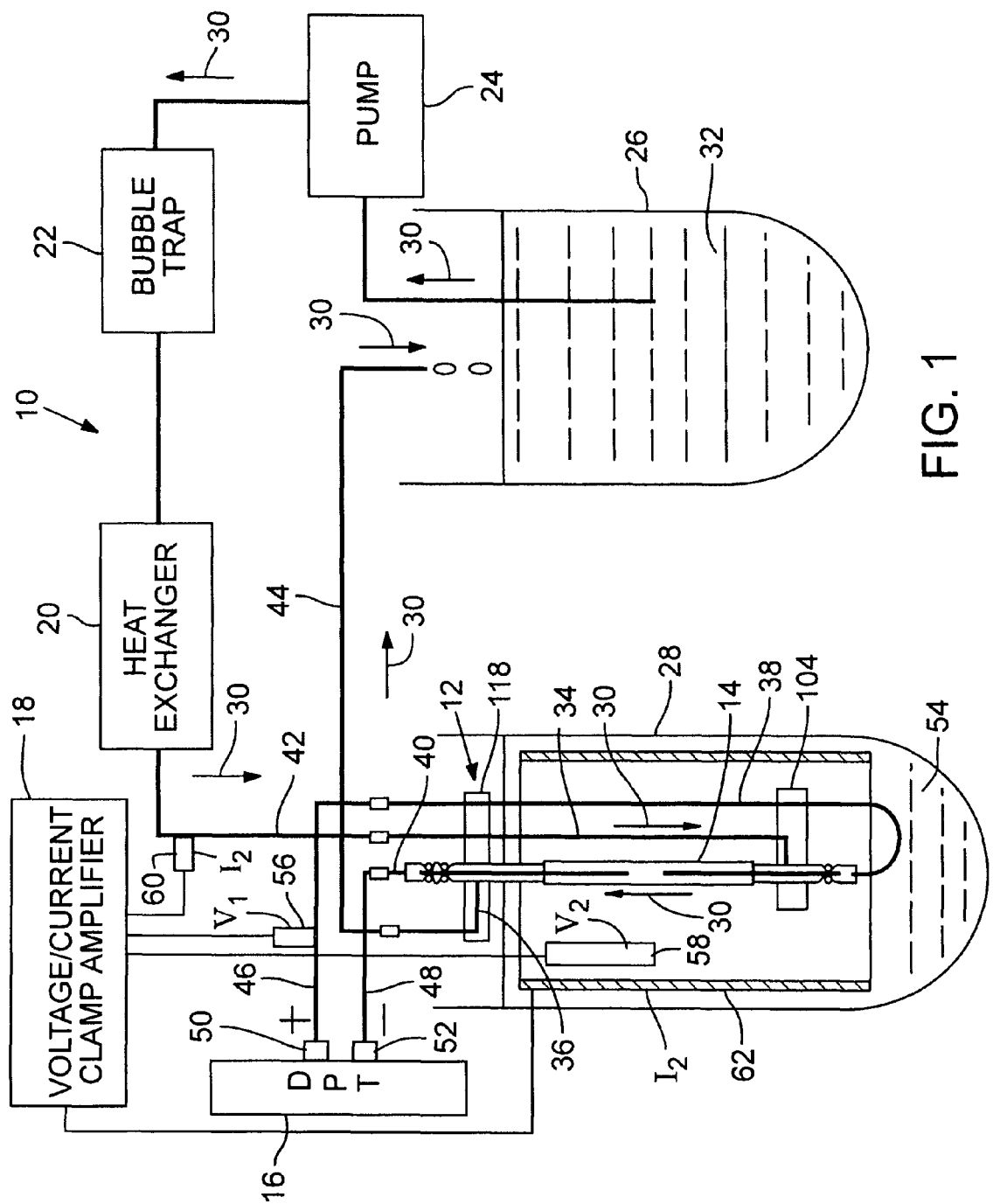
FIG. 1 is a schematic diagram of an apparatus for measuring physiological characteristics of an intact trachea in vitro, according to one embodiment.

In accordance with one embodiment, FIG. 1 shows an apparatus for measuring physiological characteristics of an intact trachea in vitro, indicating generally at 10. The apparatus 10 in the illustrated embodiment generally includes a perfusion device 12 for mounting an intact trachea 14, a differential pressure transducer 16, a voltage/current clamp amplifier 18 (or equivalent instrumentation), a heat exchanger 20, a bubble trap 22, a pump 24, a vessel 26 containing an intraluminal perfusion liquid, and a vessel 28 containing the perfusion device. A perfusion circuit for flowing a perfusion liquid (e.g., a physiological salt solution) through the trachea 14 is formed by the perfusion device 12, the heat exchanger 20, the bubble trap 22, the pump 24, and the vessel 26. The perfusion device 12 and the trachea 14 are disposed in an extraluminal bath 54 contained in vessel 28. Desirably, vessel 28 contains a sufficient volume of liquid 54 to completely submerge the trachea 14 (although it is not required to completely submerge the perfusion device 12). The trachea 14 can be a whole or substantially whole trachea or a portion of a trachea that defines a lumen (i.e., the trachea has not been cut lengthwise and flattened). Vessels 26, 28 can be jacketed type vessels having an outer jacket configured to receive a heating fluid (e.g., water) for maintaining the perfusion liquid and the extraluminal bath at a desired temperature.

In use, perfusion liquid 32 from vessel 26 is circulated through the perfusion circuit by the pump 24 in the direction of arrows 30. Agents can be added to the perfusion liquid 32 (via vessel 26) and/or to the extraluminal bath 54 in vessel 28 to evaluate or measure their bioelectric and/or mechanical effects on the trachea. Examples of such agents include, without limitation, ion channel blockers (e.g., amiloride and NPPB), ion transport inhibitors (e.g., ouabain and bumetanide), receptor agonists (e.g., histamine and terbutaline), and osmolytes (e.g., NaCl and D-mannitol (D-M)). The heat exchanger 20 is used to heat the perfusion liquid to a desired temperature prior to entering the trachea. The bubble trap 22 removes any air bubbles from the perfusion circuit.

The perfusion device 12 includes a first, perfusion liquid inlet conduit 34 for introducing perfusion liquid from the perfusion circuit into the trachea 14, a second, perfusion liquid outlet conduit 36 for discharging perfusion liquid from the perfusion device 12, a third conduit 38, and a fourth conduit 40. The first conduit 34 is fluidly connected to the perfusion circuit by a conduit 42 that is connected to the outlet of the heat exchanger 20. The second conduit 36 is fluidly connected to the perfusion circuit by a conduit 44 that introduces circulating perfusion liquid into vessel 26. Thus, perfusion liquid from the heat exchanger 20 is caused to flow through conduit 42, inlet conduit 34, the trachea 14, discharge conduit 36, conduit 44 and into vessel 26.

A first port 50 of the differential pressure transducer 16 is in fluid communication with the inlet of the trachea 14 by the third conduit 38 of the perfusion device and a conduit 46. A second port 52 of the differential pressure transducer 16 is in fluid communication with the outlet of the trachea 14 by the fourth conduit 40 and a conduit 48. As described in greater detail below, this arrangement allows the differential pressure transducer 16 to measure a pressure difference of the perfusion liquid flowing through the trachea 14.

As further shown in FIG. 1, the apparatus 10 also includes a set of voltage-sensing electrodes for measuring the transepithelial potential difference of the trachea 14. The set of voltage-sensing electrodes in the illustrated embodiment includes at least a first voltage-sensing electrode ($V_1$) 56 extending into conduit 46 so as to be in electrical continuity with the perfusion liquid therein and a second voltage-sensing electrode ($V_2$) 58 disposed in the extraluminal bath 54. The voltage-sensing electrodes 56, 58 are electrically connected to the amplifier 18. The voltage-sensing electrodes 56, 58 can be conventional half-cell electrodes, such as flowing or non-flowing half-cell electrodes, in continuity through a physiological salt solution bridge. For example, the voltage-sensing electrodes 56, 58 can be conventional silver/silver-chloride electrodes (for example, model EKC voltage electrodes from World Precision Instruments, Sarasota, Fla., or equivalent voltage electrodes available from Warner Instruments, Hamden, Conn.).

The apparatus 10 also includes a set of current electrodes for applying a current across the trachea wall. The set of current electrodes in the illustrated embodiment includes at a first current electrode ($I_1$) 60 extending into conduit 42 so as to be in electrical continuity with the perfusion liquid flowing into the trachea 14 and a second current electrode ($I_2$) 62 disposed in the extraluminal bath 54. The first current electrode 60 can be a conventional half-cell electrode, such as a conventional silver/silver-chloride electrode (for example, model EKC voltage electrodes from World Precision Instruments, Sarasota, Fla., or equivalent voltage electrodes available from Warner Instruments, Hamden, Conn.). The second current electrode 62 desirably completely surrounds the trachea 14 and the second voltage-sensing electrode 58, and can be made of any suitable, preferably non-toxic, electrically-conductive material, such as a metal or metal alloy. In particular embodiments, for example, the second current electrode 62 comprises a cylindrical platinum screen.

Figure 7:
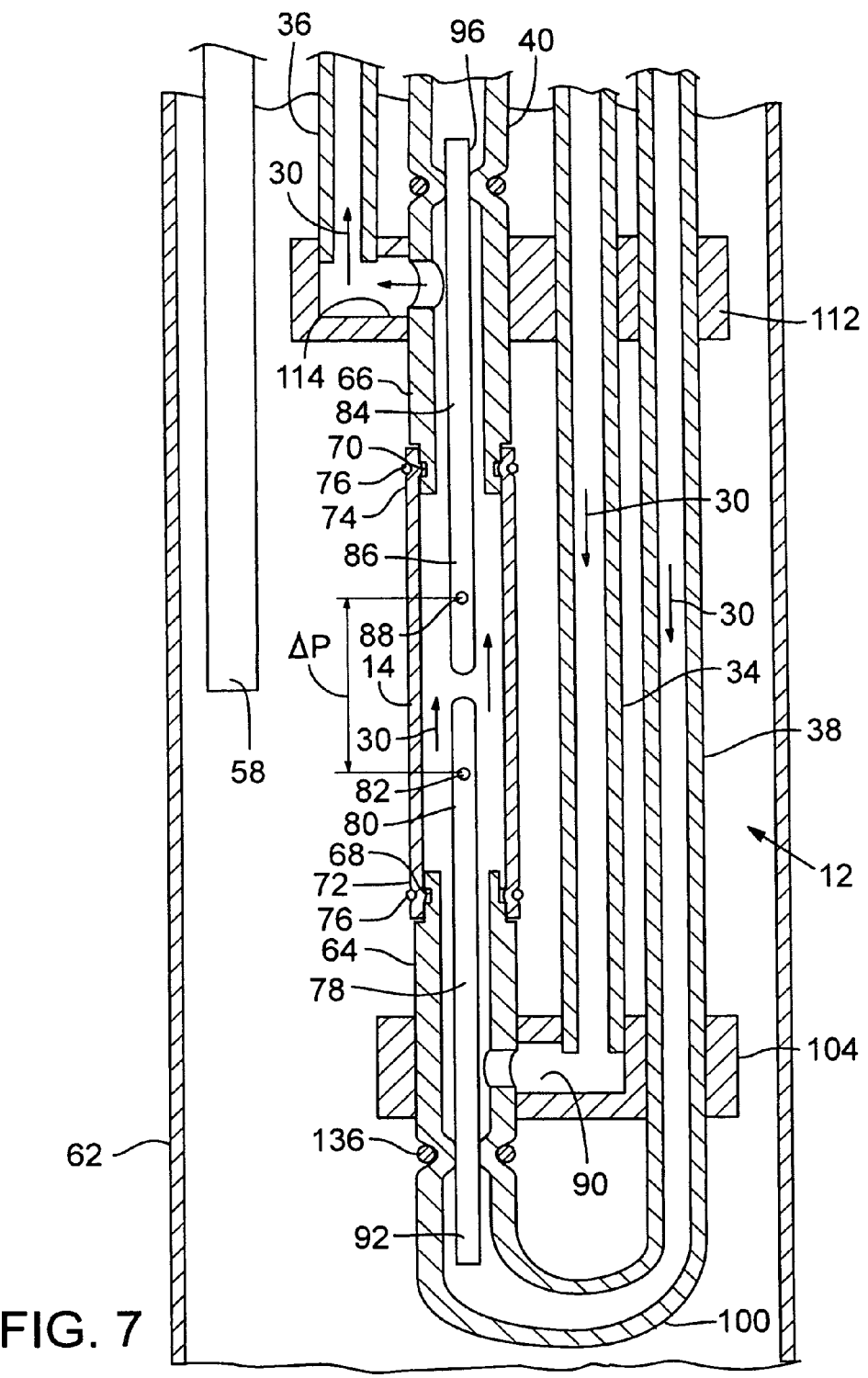
FIG. 7 is an enlarged, fragmentary view of the perfusion device, extraluminal voltage electrode, and extraluminal current electrode of the apparatus shown in FIG. 1.

Referring to FIG. 7, the perfusion device 12 includes an inlet portion 64 and an outlet portion 66 longitudinally spaced from and aligned with the inlet portion 64. The inlet portion 64 is formed with a stepped outer surface 68 and the outlet portion 66 is formed with a stepped outer surface 70. A first end portion 72 of the trachea 14 extends over the stepped surface 68 and can be secured to the inlet portion 64 by a piece of string tied tightly around the trachea 14 at the stepped surface 68. Likewise, a second end portion 74 of the trachea 14 extends over stepped surface 70 and can be secured to the outlet portion 66 by a piece of string 76 tied tightly around the trachea at the stepped surface 70.

Figure 5:
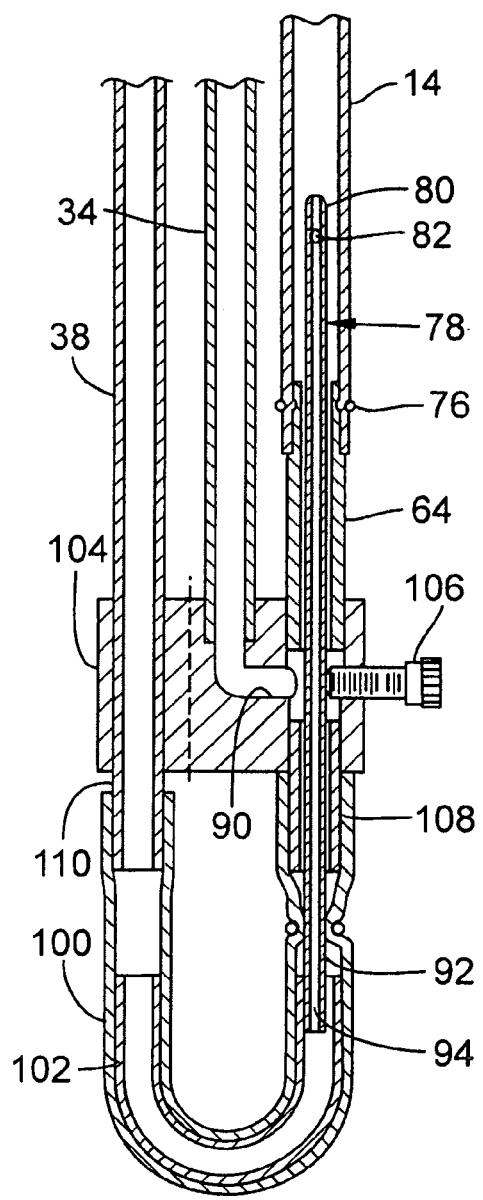
FIG. 5 is a "flattened" cross-sectional view of the perfusion device taken along section 5-5 of FIG. 3.
Figure 6:
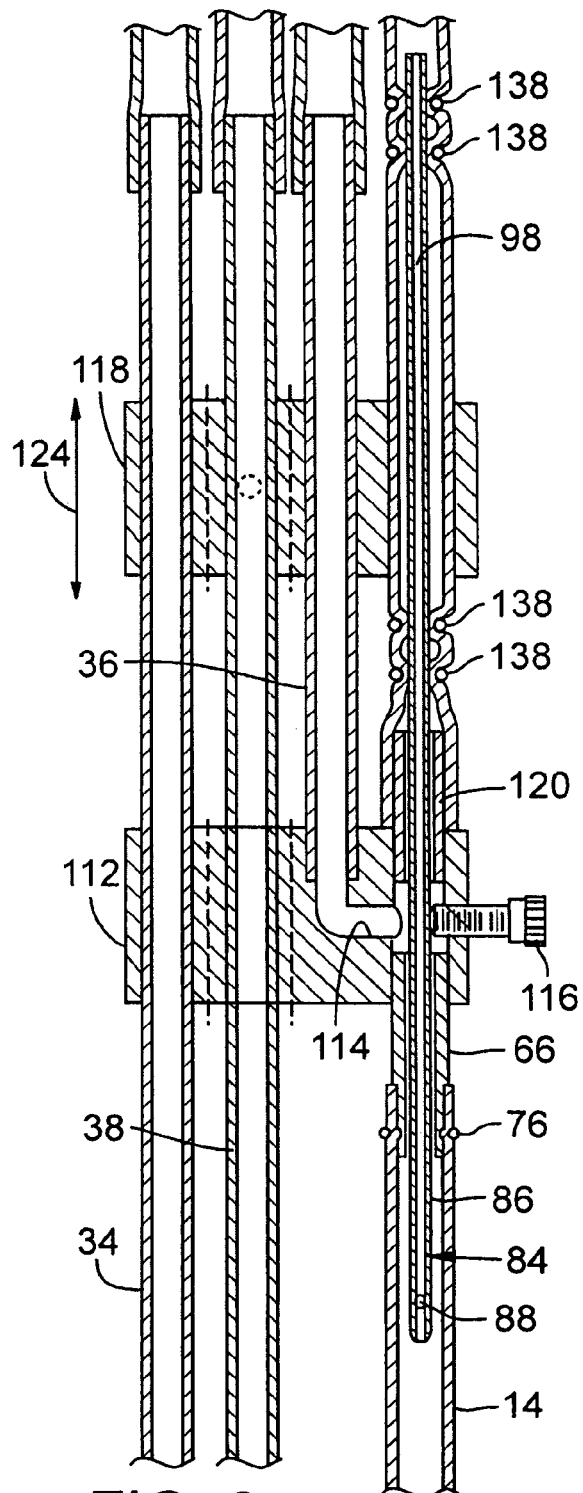
FIG. 6 is a "flattened" cross-sectional view of the perfusion device taken along section 6-6 of FIG. 4.

Referring also to FIGS. 2-6, a first cannula 78 extends coaxially through the inlet portion 64 and has a distal end portion 80 extending outwardly from the inlet portion 64 and into the first end portion 72 of the trachea 14. The first cannula 78 is formed with a lumen 94 (FIGS. 3 and 5) and two openings 82 on opposite sides of the distal portion 80 (one of which is shown in FIGS. 2 and 5), which open the lumen 94 to the perfusion liquid in the trachea for measuring the pressure of the liquid at that location. A second cannula 84 extends coaxially through the outlet portion 66 and has a distal end portion 86 extending outwardly from the outlet portion 66 and into the second end portion 74 of the trachea 14. The second cannula 84 is formed with a lumen 98 (FIGS. 4 and 6) and two openings 88 on opposite sides of the distal portion 86 (one of which is shown in FIGS. 2 and 6), which open the lumen 98 to the perfusion liquid in the trachea for measuring the pressure of the liquid at that location.

As best shown in FIGS. 5 and 7, inlet conduit 34 extends into a first manifold 104 and is fluidly connected to a bore, or passageway, 90 formed in the manifold 104. The bore 90 in turn is fluidly connected to the inlet portion 64. An inlet flow path for the perfusion liquid 32 flowing into the trachea 14 therefore is defined by bore 90 and the area between the outer surface of the first cannula 78 and the inside surface of the inlet portion 64. A removable screw 106 (FIGS. 3 and 5) is inserted into a threaded opening that is formed in the side of the manifold 104 and opens into the bore 90. The screw 106 can be removed from the manifold 104 for flushing and cleaning the device.

As best shown in FIG. 5, a tube 108 extends from the bore 90 opposite the inlet portion 64 and outwardly from the first manifold 104. Conduit 38 extends through the first manifold 104 and has a lower end portion 110 adjacent tube 108. The first cannula 78 has a proximal end portion 92 that extends through tube 108 and into a tube 100. Tube 100 has one end portion fluidly connected to tube 108 and another end portion fluidly connected to the lower end portion 110 of conduit 38. The proximal end of the first cannula 78 is open so that fluid in the trachea 14 can flow through openings 82, lumen 94, tube 100, conduit 38, and to the first port 50 of the differential pressure transducer 16 (FIG. 1). Tube 100 is compressed against the first cannula 78 below the inlet portion 64 to form a circumferential seal around the cannula, preventing perfusion liquid flowing into the inlet portion 64 from flowing directly into tube 100. This can be accomplished by tying a string or wire 136 around tubing 100, causing it to compress against the outer surface of the cannula 78. A relatively stiffer inner tube 102 can be positioned inside tube 100 to maintain tube 100 in an open bore configuration.

As best shown in FIG. 6, outlet conduit 36 extends into a second manifold 112 and is fluidly connected to a bore, or passageway, 114 formed in the manifold 112. The bore 114 in turn is fluidly connected to the outlet portion 66. An outlet flow path for the perfusion liquid 32 flowing out of the trachea 14 therefore is defined by the area between the outer surface of the second cannula 84 and the inside surface of the outlet portion 66. A removable screw 116 (FIGS. 4 and 6) is inserted into a threaded opening that is formed in the side of the second manifold 112 and opens into the bore 114. The screw 116 can be removed from the manifold 112 for flushing and cleaning the device.

Mounted adjacent the second manifold 112 is an adjustment mechanism 118 that is operable to adjust the spacing between the inlet and outlet portions 64, 66. Conduits 34 and 38 extend through the second manifold 112 and the adjustment mechanism 118. Outlet conduit 36 extends outwardly from the manifold 112 and through the adjustment mechanism 118. Conduit 40 extends through the adjustment mechanism 118 and has a lower end portion connected to a tube 120 between the adjustment mechanism 118 and the manifold 112. Tube 120 extends from bore 114 opposite the outlet portion 66 and outwardly from the manifold 112.

The adjustment mechanism 118 is maintained at a fixed position relative to the manifold 112 but is slidable relative to conduits 34, 36, 38, and 40. Additionally, manifold 112 is slidable relative to conduits 34 and 38. Hence, the adjustment mechanism 118 and manifold 112 can be moved longitudinally toward and away from manifold 104, as indicated by double-headed arrow 124, so as to increase or decrease the distance between the inlet portion 64 and the outlet portion 66 to accommodate tracheas of varying lengths. In this manner, the trachea 14 can be secured to the inlet and outlet portions 64, 66 and extended to its in situ length.

One or more set screws 126, 128 (FIG. 2) can be provided to fix the position of the adjustment mechanism 118 relative to conduits 34, 36, 38, and 40. Screw 126 extends into a threaded opening in the adjustment mechanism 118 and bears against conduit 36. Similarly, screw 128 extends into a threaded opening in the adjustment mechanism 118 and bears against conduit 38. Tightening the screws 126, 128 against conduits 36, 38, respectively, retains the adjustment mechanism 118 and manifold 112 at fixed location relative to the inlet portion 64, while loosening the screws allows adjustment of the adjustment mechanism 118 and manifold 112.

As best shown in FIG. 6, the second cannula 84 extends coaxially through tube 120 and conduit 40. The proximal end of the second cannula 84 is open so that fluid in the trachea 14 can flow through openings 88, lumen 98, conduit 40, and to the second port 52 of the differential pressure transducer 16 (FIG. 1). Conduit 40 is compressed against the second cannula 84 on opposite sides of the adjustment 118 to form circumferential seals around the cannula 84, preventing perfusion liquid flowing out of the outlet portion 66 from flowing directly into conduit 40. This can be accomplished by tying a string or wire 138 around tubing 122 at one or more locations as shown in the illustrated embodiment, causing it to compress against the outer surface of the cannula 84.

As described above, the first port 50 of the differential pressure transducer 16 is in fluid communication with the openings 82 in the first cannula 78 and the second port 52 of the differential pressure transducer 16 is in fluid communication with the openings 88 in the second cannula 84. As a result, the differential pressure transducer 16 "sees" the pressure of the perfusion liquid flowing through the trachea 14 at the openings 82 and 88 and can calculate the pressure drop ($\Delta P$) of the perfusion liquid between these two locations (as depicted in FIG. 7). The pressure drop is a direct index of the airway diameter when the trachea is perfused at a constant flow, and hence is a measure of smooth muscle relaxation or contraction.

Other types of differential pressure devices also can be used to determine $\Delta P$. In one embodiment, for example, each of the cannulas 78, 84 can be fluidly connected to a respective pressure transducer. Each pressure transducer measures the pressure at a location in the trachea and $\Delta P$ is calculated from these measurements. In other embodiments, a mechanical differential pressure gauge (or two separate pressure gauges) can be used instead of a differential pressure transducer.

Under open circuit conditions, the first current electrode 60 (FIG. 1) introduces an electrical current into the perfusion liquid flowing into the perfusion device 12. The electrical current flows into the perfusion device, where it emanates from the inlet portion 64 (FIG. 7) and flows across the trachea wall to the second current electrode 62. The first voltage-sensing electrode 56 (FIG. 1) is in electrically continuity with the perfusion liquid in the trachea 14 (via cannula 78, tube 100, and conduits 38 and 46) and therefore senses the electrical potential inside the trachea. The second voltage-sensing electrode 58 senses the electrical potential in the extraluminal bath 54 outside of the trachea. The amplifier 18 calculates the electrical potential difference between the voltage-sensing electrodes 56, 58, which represents the transepithelial potential difference of the trachea. The amplifier 18 can also calculate the transepithelial impedance across the trachea wall based on the applied current and the measured potential difference. Hence, the apparatus 10 allows for simultaneous evaluation of smooth muscles activity and bioelectric properties of the trachea, including the transepithelial potential difference and the transepithelial impedance.

In an alternative approach, the apparatus 10 can be used in a "voltage clamp" (short circuit) mode where calibrated voltage pulses are applied to the electrodes 56, 58 and the changes in short circuit current between electrodes 60, 62 are measured to determine the transepithelial impedance across the trachea wall.

In alternative embodiments, separate devices can be used measure voltage, generate the electrical current, and/or measure impedance. For example, separate electrometers can be used to measure voltage, generate the electrical current, and measure impedance. Alternatively, an electrometer can be used measure voltage and generate the electrical current, while a computer or other controller calculates impedance based on the voltage and current.

EXAMPLE

Hartley guinea pigs were anesthetized by i.p. injection of sodium pentobarbital (65 mg/kg). A 4.2-cm tracheal segment was removed and mounted on a perfusion device 12 at its in situ length. The perfusion device was placed in an extraluminal bath containing a modified Krebs-Henseleit (OH) solution, and was perfused at 24 ml/min with MKH solution from an intraluminal bath. Water was used as a heat transfer fluid and was supplied to the heat exchanger 20 and the outer jackets of vessels 26, 28 to maintain the temperature of the extraluminal and intraluminal baths at about 37° C. Current pulses (20 µA, 5 s duration, 50 s intervals) were delivered through the current electrodes, while the changes in the transepithelial potential difference ($V_t$) caused by the current pulses were monitored under open-circuit conditions. Alternatively, and as mentioned above, voltage pulses can be applied across the voltage electrodes under voltage-clamp conditions, while the changes in short circuit current are monitored.

The preparation was equilibrated for 2.5 hours to allow $V_t$ and the pressure drop ($\Delta P$) to stabilize before the current pulses were delivered. Basal $V_t$ (the transepithelial voltage in the basal, or steady, state of an unstimulated epithelium) was 14.8±0.8 mV. Relaxation responses of the smooth muscle were observed by pre-contracting the trachea with methacholine (MCh, $3\times10^{-7}$M, $EC_{50}$) in the extraluminal bath, which induced transepithelial hyperpolarization. To determine the effects of relaxant agents, when the mechanical and bioelectric responses reached their plateau responses to MCh, the trachea was treated with agents added to the extraluminal or intraluminal bath. The agents used in this example are described in tables 1 and 2 below. The effects of the agents were analyzed statistically using student's paired t-test. P<0.05 was accepted as significant, and is indicated by an asterisk in FIGS. 8-15. The results are presented as means±SE. Each agent was tested four times.

TABLE 1

|  | Ion channel blockers | | Ion transport inhibitors | |
| --- | --- | --- | --- | --- |
| Agents | Amiloride | NPPB | Ouabain | Bumetanide |
| Conc. | $3 \times 10^{-5}$ M (intraluminal) | $10^{-4}$ M (intraluminal) | $10^{-5}$ M (extraluminal) | $10^{-5}$ M (extraluminal) |
| Target | $Na^+$ channel | $Cl^-$ channel | $Na^+, K^+$- pump | $Na^+, K^+, 2Cl^-$- cotransporter |

TABLE 2

|  | Receptor agonists | | Osmolytes | |
| --- | --- | --- | --- | --- |
| Agents | Histamine | Terbutaline | NaCl | D-M |
| Conc. | $7.4 \times 10^{-6}$ M (extraluminal) | $10^{-7}$ M (extraluminal) | 300 mosM (intraluminal) | 300 mosM (intraluminal) |
| Target | $H_1$ | $\beta_2$ | epithelium | epithelium |

Amiloride, NPPB and bumetanide were dissolved in dimethyl sulfoxide (DMSO) (with a final concentration equal to or less than 0.04%). The other agents were prepared in MKH. Terbutaline, histamine, ouabain and bumetanide were added to the extraluminal bath; the other agents were added to the intraluminal bath. Hyperosmolar solutions were prepared by adding osmolytes to MKH solution.

Figure 8B:
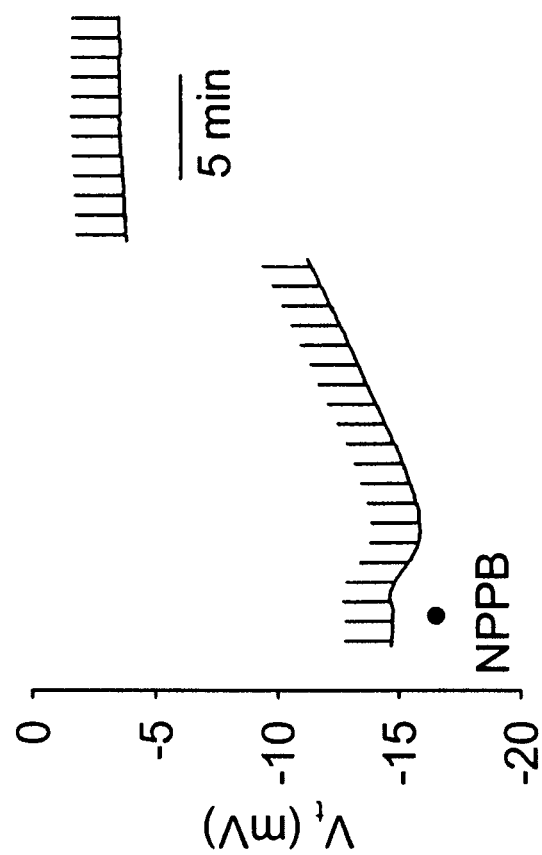
FIGS. 8A and 8B are data plots showing the effects of amiloride and NPPB, respectively, on the transepithelial potential difference ($V_t$) of a trachea. The vertical lines extending above the data plots show the voltage excursions in response to the application of a calibrated current across the trachea wall.
Figure 8A:
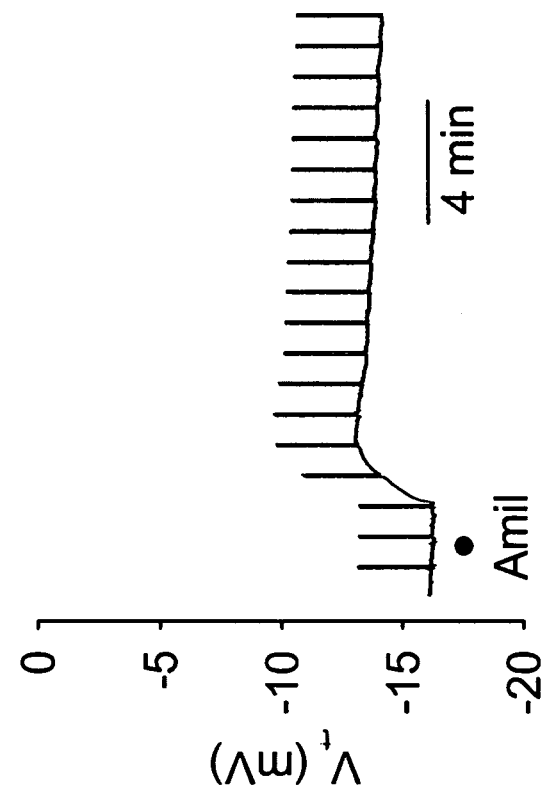
Figure 9A:
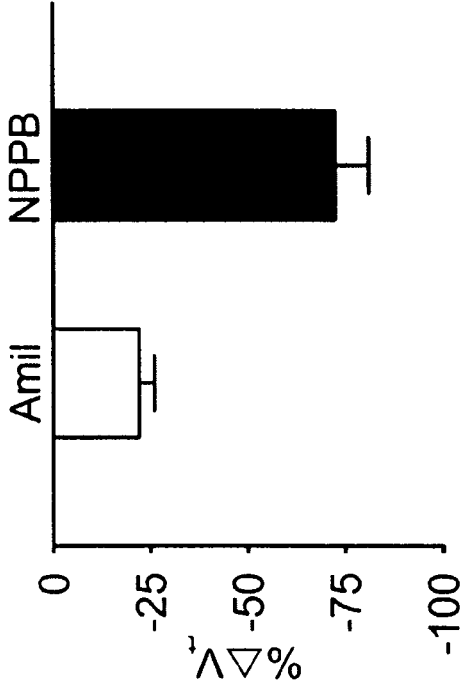
FIGS. 9A to 9D are bar graphs summarizing the effects of amiloride and NPPB on $V_t$ and the transepithelia impedance ($R_t$) of the trachea.
Figure 9B:
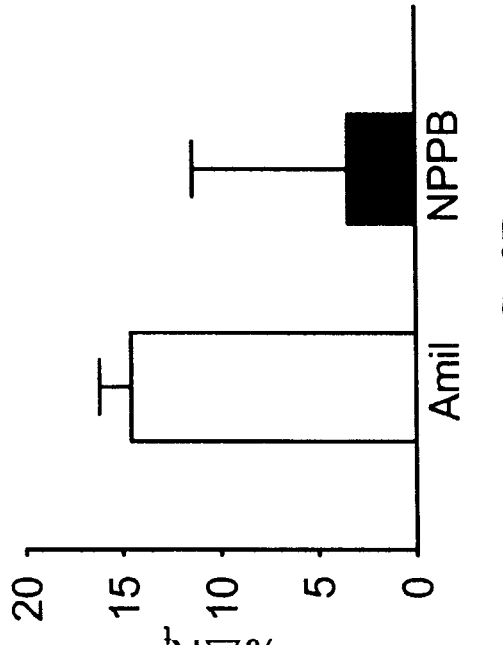
Figure 9C:
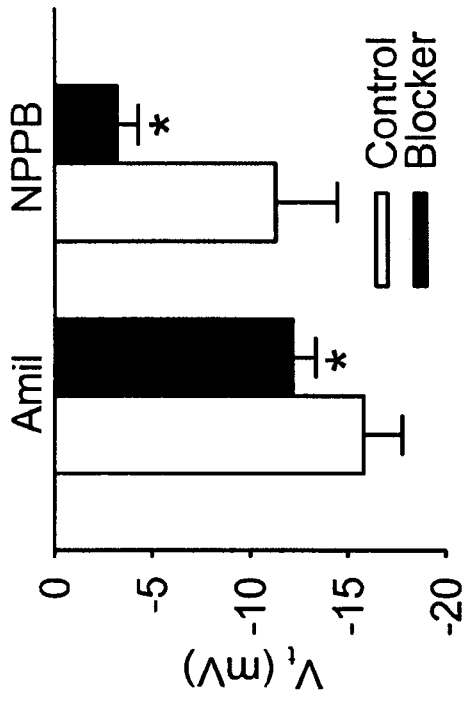
Figure 9D:
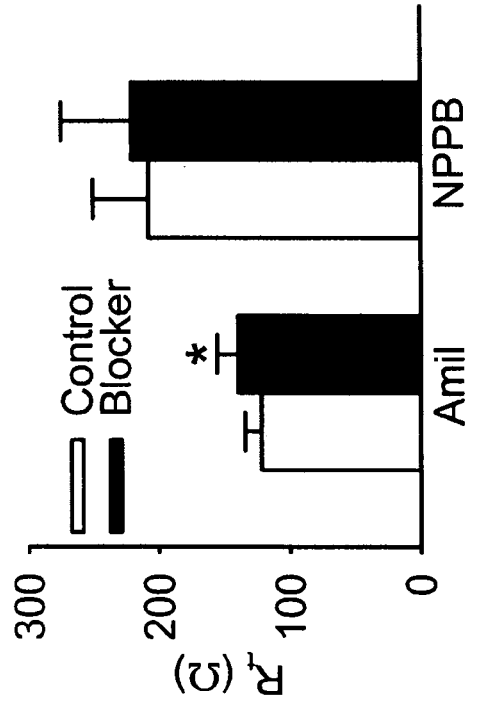
Figure 11A:
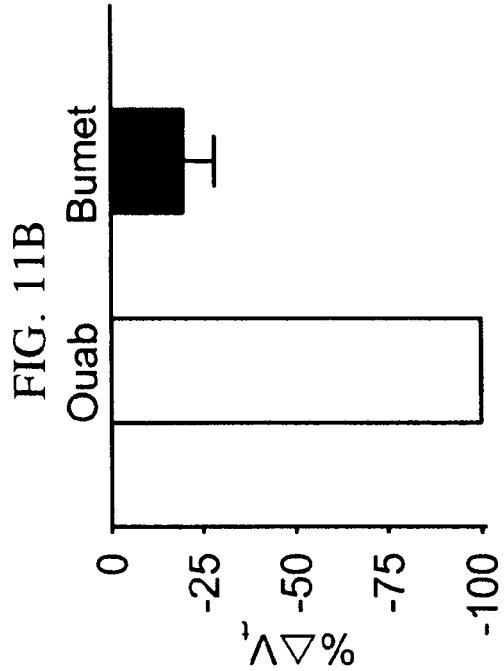
FIGS. 11A to 11D are bar graphs summarizing the effects of ouabain and bumetanide on $V_t$ and $R_t$ of the trachea.
Figure 11B:
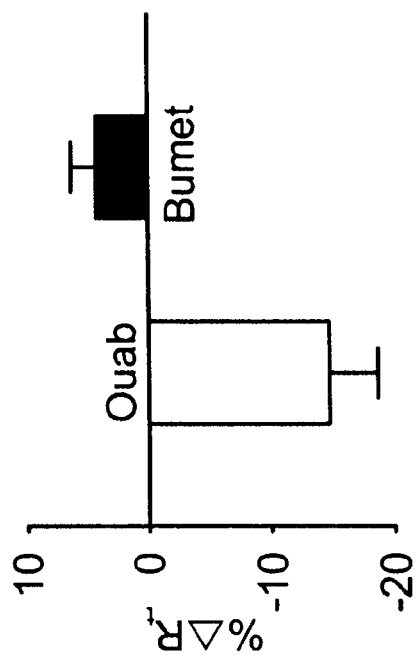
Figure 11C:
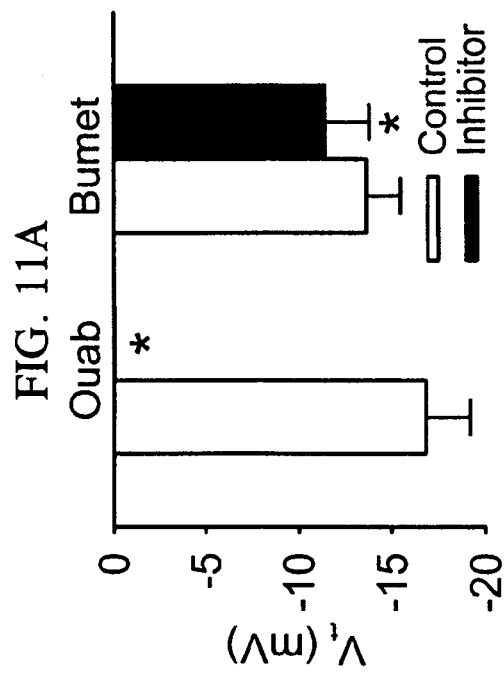
Figure 11D:
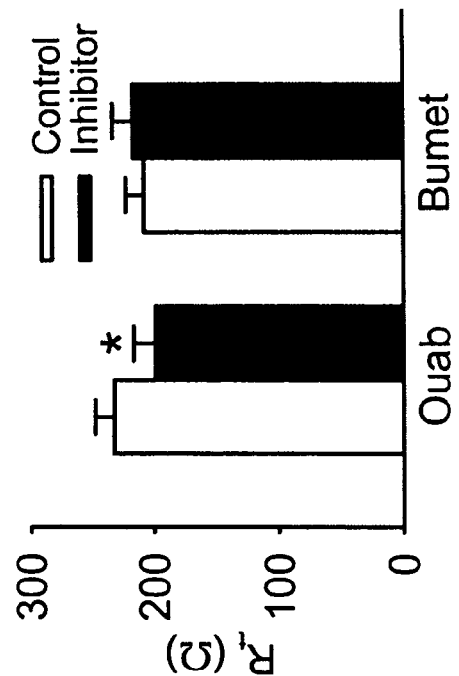

FIGS. 8A and 8B show the effects of amiloride and NPPB on $V_t$. Both agents caused depolarization of the epithelium, though depolarization caused by NPPB was slower to develop and greater in magnitude. Neither agent affected ΔP. FIGS. 9A-9D are bar graphs summarizing the effects of amiloride and NPPB on $V_t$ and $R_t$. The open bars in FIGS. 9A and 9C represent $V_t$ and $R_t$ before the agents were added. The depolarization caused by amiloride was accompanied by an increase in $R_t$, while NPPB had a negligible effect on $R_t$.

FIGS. 10A-10D show the effects of ouabain and bumetanide on ΔP and $V_t$. Ouabain caused an immediate depolarization (FIG. 10C) and a delayed contraction of the trachea (FIG. 10A). Bumetanide caused depolarization (FIG. 10D) and a small degree of relaxation of the trachea (FIG. 10B). FIGS. 11A-11D are bar graphs summarizing the effects of ouabain and bumetanide on $V_t$ and $R_t$. The depolarization caused by ouabain was complete and was accompanied by a decrease in $R_t$. Bumetanide did not effect $R_t$.

FIGS. 12A and 12D show the effects of histamine and terbutaline on ΔP and $V_t$. Histamine caused contraction (FIG. 12A) and variable $V_t$ responses (FIG. 12C). Terbutaline caused relaxation (FIG. 12B) and transient depolarization in three of the four preparations followed by slow hyperpolarization (FIG. 12D). FIGS. 13A-13D are bar graphs summarizing the effects of histamine and terbutaline on $V_t$ and $R_t$. On average, histamine and terbutaline did not effect $V_t$ appreciably. Both agents did not effect $R_t$.

FIGS. 14A-14D show the effects of hyperosmolarity elicited with NaCl (300 mosM) and D-M (300 mosM) on ΔP and $V_t$. NaCl and D-M caused depolarization (FIGS. 14C and 14D) and relaxation (FIGS. 14A and 14B) in the presence MCh. FIGS. 15A-15D are bar graphs summarizing the effects of NaCl and D-M on $V_t$ and $R_t$. Both osmolytes caused depolarization. NaCl decreased $R_t$, while D-M increased $R_t$.

Because the tracheal segment remains intact and is not distorted in shape, the average basal $V_t$ was about twice as large as that measured in a conventional Ussing apparatus, which only provides $V_t$ and $R_t$ information in flattened tracheal segments. Notably, the values obtained with the device more closely represent the actual value of $V_t$ in a live animal than that which can be obtained using a conventional Ussing preparation.

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

We claim:

1. An apparatus for measuring physiological characteristics of an intact trachea in vitro, comprising:
  a perfusion device configured to flow a perfusion liquid through the trachea;
  a differential pressure device operable to measure a pressure difference of the perfusion liquid flowing through the trachea;
  a set of current electrodes comprising at least a first current electrode and a second current electrode operable to pass an applied current through the epithelium of the trachea between the first and second current electrodes; and
  a set of voltage-sensing electrodes comprising at least a first voltage-sensing electrode and a second voltage-sensing electrode operable to detect a transepithelial potential difference between the voltage-sensing electrodes;
  a vessel containing an extraluminal bath and adapted to receive the trachea in the bath;
  wherein the first voltage electrode is in electrical continuity with the perfusion liquid flowing and the second voltage electrode is disposed in the extraluminal bath; and
  wherein the first current electrode is in electrical continuity with the perfusion liquid and the second current electrode is disposed in the extraluminal bath wherein the second current electrode completely surrounds the perfusion device and the second voltage electrode.

2. The apparatus of claim 1, wherein the second current electrode comprises a metal screen.

3. The apparatus of claim 1, wherein the perfusion device comprises:
an inlet portion adapted to introduce the perfusion liquid into a first end of the trachea and an outlet portion adapted to receive the perfusion liquid flowing outwardly from a second end of the trachea;
a first, inlet conduit in fluidic communication with the inlet portion and adapted to introduce the perfusion liquid into the inlet portion;
a second conduit in fluidic communication with the inlet portion and fluidly connected to the differential pressure device for measuring the pressure of the perfusion liquid flowing from the inlet portion and into the trachea;
a third, outlet conduit in fluidic communication with the outlet portion and adapted receive the perfusion liquid flowing from the outlet portion;
a fourth conduit in fluidic communication with the outlet portion and fluidly connected to the differential pressure device for measuring the pressure of the perfusion liquid flowing from the trachea and into the outlet portion.

4. The apparatus of claim 3, further comprising:
wherein the first current electrode is in electrical continuity with the perfusion liquid flowing through the first conduit; and
wherein the first voltage electrode is in electrical continuity with the perfusion liquid in the second conduit.

5. The apparatus of claim 3, wherein the perfusion device further comprises:
an inlet cannula having a lumen, a proximal end portion in the inlet portion and a distal end portion extending outwardly from the inlet portion and adapted to extend into the first end of the trachea, the distal end portion having at least one opening;
an outlet cannula spaced from and aligned with the inlet cannula, the outlet cannula having a lumen, a proximal end portion in the outlet portion and a distal end portion extending outwardly from the outlet portion and adapted to extend into the second end of the trachea, the distal end portion having at least one opening;
wherein the first conduit and the inlet portion define an inlet flow path for the perfusion liquid between an outer surface of the inlet cannula and an inner surface of inlet portion;
wherein the second conduit is in fluidic communication with the lumen of the inlet cannula at the proximal end thereof and the differential pressure device;
wherein the third conduit and the outlet portion define an outlet flow path for the perfusion liquid between an outer surface of the outlet cannula and an inner surface of the outlet portion;
wherein the fourth conduit is in fluidic communication with the lumen of the outlet cannula at the proximal end thereof and the differential pressure device; and
wherein the differential pressure device measures the pressure difference of the perfusion liquid between the opening in the distal end portion of the inlet cannula and the opening in the distal end portion of the outlet cannula.

6. The apparatus of claim 1, further comprising voltage-measuring means for measuring the transepithelial potential difference between the voltage electrodes.

7. The apparatus of claim 6, further comprising current-generating means for generating the applied current to the current electrodes.

8. The apparatus of claim 7, wherein the voltage-measuring means and the current-generating means comprise a voltage/current clamp amplifier.

9. An apparatus for measuring physiological characteristics of an intact trachea in vitro, comprising:
means for perfusing a perfusion liquid through the trachea;
means for measuring a pressure difference of the perfusion liquid flowing through the trachea;
means for passing a current through the wall of the trachea;
means for measuring a transepithelial potential difference of the trachea; and
means for determining the impedance of the trachea based on the current and the transepithelial potential difference;
wherein the means for measuring a transepithelial potential difference of the trachea comprises a first voltage-sensing electrode in electrical continuity with the perfusion liquid and a second voltage-sensing electrode disposed in a liquid surrounding the trachea;
wherein the means for passing a current through the wall of the trachea comprises a first current electrode in electrical continuity with the perfusion liquid and a second current electrode disposed in the liquid surrounding the trachea, the second current electrode completely surrounding the second voltage-sensing electrode.

10. The apparatus of claim 9, wherein the means for measuring a transepithelial potential difference of the trachea further comprises a voltage-measuring device operable to measure the transepithelial potential difference by measuring the potential difference between the voltage-sensing electrodes.

11. The apparatus of claim 10, wherein the means for passing a current through the wall of the trachea further comprises a current generator operable to generate and cause the current to flow from the first current electrode through the trachea wall to the second current electrode.

12. The apparatus of claim 11, wherein the second current electrode comprises a metal screen completely surrounding the second voltage-sensing electrode.

13. The apparatus of claim 9, wherein the means for perfusing a perfusion liquid through the trachea comprises a perfusion circuit that circulates a perfusion liquid through the trachea, the perfusion circuit comprising a trachea-mounting mechanism that includes an inlet portion and an outlet portion, wherein the inlet portion is adapted to be secured to a first end of the trachea and the outlet portion is adapted to be secured to a second end of the trachea such that circulating perfusion liquid can flow into the trachea via the inlet portion and out of the trachea via the outlet portion.

14. A method for measuring physiological characteristics of an intact trachea in vitro, comprising:
flowing a perfusion liquid through the trachea;
measuring a transepithelial potential difference of the trachea;
passing an electrical signal through the wall of the trachea; and
measuring an electrical impedance of the trachea;
wherein the trachea is placed in an extraluminal bath;
wherein measuring the transepithelial potential difference comprises measuring the electrical potential between first and second voltage-sensing electrodes, the first voltage-sensing electrode being in electrical continuity with the perfusion liquid flowing into the trachea and the second voltage-sensing electrode is disposed in the extraluminal bath;
wherein passing an electrical signal through the wall of the trachea comprises placing a first current electrode in electrical continuity with the perfusion liquid flowing into the trachea, placing a second current electrode in the extraluminal bath such that the second current electrode completely surrounds the second voltage-sensing electrode, and applying the electrical signal to the first current electrode such that the electrical signal is transmitted through the trachea wall to the second current electrode.

15. The method of claim 14, further comprising measuring a pressure difference of the perfusion liquid flowing through the trachea.

16. The method of claim 15, wherein the transepithelial potential difference, the electrical impedance, and the pressure difference are measured simultaneously.

17. The method of claim 14, further comprising:
adding an agent to the perfusion liquid; and
determining the change in the transepithelial potential difference and the electrical impedance caused by the addition of the agent.

18. The method of claim 17, further comprising:
prior to adding the agent to the perfusion liquid, measuring a pressure difference of the perfusion liquid flowing through the trachea; and
determining the change in the pressure difference caused by the addition of the agent.

19. The method of claim 14, further comprising:
adding an agent to the extraluminal bath; and
determining the change in the transepithelial potential difference and the electrical impedance caused by the addition of the agent.

20. The method of claim 19, further comprising:
prior to adding the agent to the extraluminal bath, measuring a pressure difference of the perfusion liquid flowing through the trachea; and
determining the change in the pressure difference caused by the addition of the agent.

21. An apparatus for measuring physiological characteristics of an intact trachea in vitro, comprising:
a perfusion device configured to flow a perfusion liquid through the trachea;
a vessel containing an extraluminal bath and adapted to receive the trachea in the bath;
a differential pressure device operable to measure a pressure difference of the perfusion liquid flowing through the trachea;
a set of voltage-sensing electrodes comprising a first voltage-sensing electrode in electrical continuity with the perfusion liquid and a second voltage-sensing electrode disposed in the extraluminal bath;
a voltage-measuring device operable to measure a transepithelial potential difference of the trachea by measuring electrical potential between the voltage-sensing electrodes;
a set of current electrodes comprising a first current electrode in electrical continuity with the perfusion liquid and a second current electrode disposed in the extraluminal bath and completely surrounding the trachea and the second voltage-sensing electrode; and
a current generator connected to the current electrodes and operable to generate a current that passes through the epithelium of the trachea between the first and second current electrodes.

22. The apparatus of claim 21, wherein the perfusion device comprises:
an inlet portion adapted to be secured to a first end of the trachea and an outlet portion adapted to be secured to a second end of the trachea so that perfusion liquid can flow into the first end of the trachea via the inlet portion and out of the second end of the trachea via the outlet portion;
a first, inlet conduit in fluidic communication with the inlet portion for introducing the perfusion liquid into the inlet portion and the trachea;
a second conduit in fluidic communication with the inlet portion and the differential pressure device for measuring the pressure of the perfusion liquid at a first location in the trachea;
a third, outlet conduit in fluidic communication with the outlet portion and adapted receive the perfusion liquid from the outlet portion;
a fourth conduit in fluidic communication with the outlet portion and the differential pressure device for measuring the pressure of the perfusion liquid at a second location in trachea downstream of the first location.

* * * * *